United States Patent
Sheng et al.

(10) Patent No.: US 11,033,760 B2
(45) Date of Patent: Jun. 15, 2021

(54) SYSTEMS AND METHODS FOR DELIVERING RADIOTHERAPY

(71) Applicant: The Regents of the University of California, Oakland, CA (US)

(72) Inventors: Ke Sheng, Los Angeles, CA (US); Salime M. Boucher, Santa Monica, CA (US)

(73) Assignees: The Regents of the University of California, Oakland, CA (US); Radiabeam Systems, LLC, Santa Monica, CA (US)

(*) Notice: Subject to any disclaimer, the term of this patent is extended or adjusted under 35 U.S.C. 154(b) by 0 days.

(21) Appl. No.: 16/496,982

(22) PCT Filed: Mar. 24, 2018

(86) PCT No.: PCT/US2018/024216
§ 371 (c)(1),
(2) Date: Sep. 24, 2019

(87) PCT Pub. No.: WO2018/176016
PCT Pub. Date: Sep. 27, 2018

(65) Prior Publication Data
US 2020/0094078 A1    Mar. 26, 2020

Related U.S. Application Data

(60) Provisional application No. 62/476,287, filed on Mar. 24, 2017.

(51) Int. Cl.
*A61N 5/10* (2006.01)
*A61N 5/06* (2006.01)

(52) U.S. Cl.
CPC .......... *A61N 5/1083* (2013.01); *A61N 5/1031* (2013.01); *A61N 2005/0626* (2013.01)

(58) Field of Classification Search
CPC ................ A61N 5/1083; A61N 5/1031; A61N 2005/0626; A61N 5/103
(Continued)

(56) References Cited

U.S. PATENT DOCUMENTS

| 5,207,223 A | 5/1993 | Adler |
|---|---|---|
| D646,703 S | 10/2011 | Wong |

(Continued)

FOREIGN PATENT DOCUMENTS

WO    2016140955 A1    9/2016

OTHER PUBLICATIONS

Atalar B, et al. Dosimetric comparison of robotic and conventional linac based stereotactic lung irradiation in early-stage lung cancer. Technol Cancer Res Treat 2012; 11: 249-255.
(Continued)

*Primary Examiner* — Courtney D Thomas
(74) *Attorney, Agent, or Firm* — Quarles & Brady LLP (57) ABSTRACT

A radiotherapy system and method for delivering radiotherapy are provided. In some aspects, the radiotherapy system includes beam director comprising a radiation source configured to generate radiation for irradiating a patient, the beam director having at least four degrees of freedom of movement. The radiotherapy system also includes a controller configured to operate the beam director to irradiate the patient in accordance with a radiation treatment plan, wherein the radiation treatment plan is generated based on a solution space determined by the at least four degrees of freedom of movement of the beam director.

20 Claims, 7 Drawing Sheets

(58) Field of Classification Search
USPC .......................................................... 378/65
See application file for complete search history.

(56) References Cited

U.S. PATENT DOCUMENTS

| | | |
|---|---|---|
| 2005/0281389 A1 | 12/2005 | Kusch |
| 2007/0071168 A1 | 3/2007 | Allison et al. |
| 2007/0230660 A1 | 10/2007 | Herrmann |
| 2010/0104068 A1* | 4/2010 | Kilby .................. A61N 5/1031 378/65 |

OTHER PUBLICATIONS

Bangert M, et al. Characterizing the combinatorial beam angle selection problem. Phys Med Biol 2012; 57: 6707-6723.
Bansal M, et al. Radiation related morbidities and their impact on quality of life in head and neck cancer patients receiving radical radiotherapy. Qual Life Res 2004; 13: 481-488.
Bjordal K, et al. Quality of life in patients treated for head and neck cancer: a follow-up study 7 to 11 years after radiotherapy. Int J Radiat Oncol Biol Phys 1994; 28: 847-856.
Brock J, et al. Optimising stereotactic body radiotherapy for non-small cell lung cancer with volumetric intensity-modulated arc therapy—a planning study. Clin Oncol (R Coll Radiol) 2012; 24: 68-75.
Brown WT, et al. Treatment of early nonsmall cell lung cancer, stage IA, by image-guided robotic stereotactic radioablation—CyberKnife. Cancer J 2007; 13: 87-94.
Chronowski GM, et al. Unilateral radiotherapy for the treatment of tonsil cancer. Int J Radiat Oncol Biol Phys 2012; 33:204-209.
Coon AB, et al. Tomotherapy and multifield intensity-modulated radiotherapy planning reduce cardiac doses in left-sided breast cancer patients with unfavorable cardiac anatomy. Int J Radiat Oncol Biol Phys 2010; 78: 104-110.
Ding C, et al. A dosimetric comparison of stereotactic body radiation therapy techniques for lung cancer: robotic versus conventional linac-based systems. J Appl Clin Med Phys 2010; 11: 3223.
Dong P, et al. 4pi Non-Coplanar Liver SBRT: a Novel Delivery Technique. Int J Radiat Oncol Biol Phys 2013; 85:1360-1366.
Dong P, et al. 4pi noncoplanar stereotactic body radiation therapy for centrally located or larger lung tumors. Int J Radiat Oncol Biol Phys 2013; 86: 407-413.
Epstein JB, et al. Quality of life and oral function in patients treated with radiation therapy for head and neck cancer. Head Neck 2001; 23: 389-398.
Grills IS, et al. Potential for reduced toxicity and dose escalation in the treatment of inoperable non-small-cell lung cancer: a comparison of intensity-modulated radiation therapy (IMRT), 3D conformalradiation, and elective nodal irradiation. Int J Radiat Oncol Biol Phys 2003;57: 875-890.
Haertl PM, et al. Treatment of left sided breast cancer for a patient with funnel chest: Volumetric modulated arc therapy vs. 3D-CRT and intensitymodulated radiotherapy. Med Dosim 2012.
Henson BS, et al. Two-year longitudinal study of parotid salivary flow rates in head and neck cancer patients receiving unilateral neck parotid-sparing radiotherapy treatment. Oral Oncol 1999; 35: 234-241.
Holt A, et al. Volumetric-modulated arc therapy for stereotactic body radiotherapy of lung tumors: a comparison with intensity modulated radiotherapy techniques. Int J Radiat Oncol Biol Phys 2011; 81: 1560-1567.
Hsieh CH, et al. Comparison of coplanar and noncoplanar intensity-modulated radiation therapy and helical tomotherapy for hepatocellular carcinoma. Radiat Oncol 2010; 5: 40.

International Searching Authority, International Search Report and Written Opinion for applicaton PCT/US2018/024216, dated Jun. 22, 2018, 12 pages.
Jellema AP, et al. Unilateral versus bilateral irradiation in squamous cell head and neck cancer in relation to patient-rated xerostomiaand sticky saliva. Radiother Oncol 2007; 85: 83-89.
Jeremic B, et al. Elective ipsilateral neck irradiation of patients with locally advanced maxillary sinus carcinoma. cancer 2000; 88: 2246-2251.
Khan AJ, et al. A dosimetric comparison of three-dimensional conformal, intensity modulated radiation therapy, and MammoSite partial-breast irradiation. Brachytherapy 2006; 5: 183-188.
Kuo YC, et al. Volumetric intensity-modulated Arc (RapidArc) therapy for primary hepatocellular carcinoma: comparison with intensity-modulated radiotherapy and 3D conformal radiotherapy. Radiat Oncol 2011; 6: 76.
Leksell L. The stereotaxic method and radiosurgery of the brain. Acta Chir Scand 1951; 102: 316-319.
Liu W, et al. Effectiveness of robust optimization in intensity-modulated proton therapy planning for head and neck cancers. Med Phys 2013; 40: 051711.
Marsh L, et al. Treatment planning for parotid sparing in the patient requiring bilateral neck irradiation. Med Dosim 1996; 21:7-13.
Mavroidis P, et al. Comparison of the 3D-conformal, helical tomotherapy and multileaf collimators-based intensity modulated radiotherapy modalities using radiobiological measures. J BUON 2008; 13: 75-86.
Mavroidis P, et al. Comparison of the helical tomotherapy against the multileaf collimator-based intensity modulated radiotherapy and 3D conformal radiation modalities inlung cancer radiotherapy. Br J Radiol 2011; 84: 161-172.
Murthy K, et al. Evaluation of dose coverage to target volume and normal tissue sparing in the adjuvant radiotherapy of gastric cancers: 3D-CRT compared with dynamic IMRT. Biomed Imaging Interv J 2010; 6:e29.
Nutting CM, et al. Optimisation of radiotherapy for carcinoma of the parotid gland: a comparison of conventional, three-dimensional conformal, and intensity-modulated techniques. Radiother Oncol 2001; 60: 163-172.
Oermann EK, et al. Low incidence of new biochemical and clinical hypogonadism following hypofractionated stereotactic body radiation therapy (SBRT) monotherapy for lowto intermediate-risk prostate cancer. J Hematol Oncol 2011; 4: 12.
Ong CL, et al. Stereotactic radiotherapy for peripheral lung tumors: a comparison of volumetric modulated arctherapy with 3 other delivery techniques. Radiother Oncol 2010; 97: 437 442.
Orton N, et al. Total scalp irradiation using helical tomotherapy. Med Dosim 2005; 30: 162-168.
O'Sullivan B, et al. The benefits and pitfalls of ipsilateral radiotherapy in carcinoma of the tonsillar region. Int J Radiat Oncol Biol Phys 2001; 51: 332-343.
Romeijn HE, et al. A column generation approach to radiation therapy treatment planning using aperture modulation. Siam J Optimiz 2005; 15: 838-862.
Rusthoven KE,et al. Freedom from local and regional failure of contralateral neck with ipsilateral neck radiotherapy for node-positive tonsil cancer: results of a prospective management approach. Int J Radiat Oncol Biol Phys 2009; 74: 1365-1370.
Thieke C, et al. Characterization of dose distributions through the max and mean dose concept. Acta Oncologica 2002; 41: 158-161.
Yin Y, et al. Dosimetric comparison of RapidArc with fixed gantry intensity-modulated radiotherapy treatment for multiple liver metastases radiotherapy. Med Dosim 2011; 36: 448-454.

* cited by examiner

SYSTEMS AND METHODS FOR DELIVERING RADIOTHERAPY

CROSS-REFERENCE TO RELATED APPLICATIONS

This application represents the national stage entry of International Application PCT/US2018/024216, filed on Mar. 24, 2018, which claims benefit of and priority to U.S. Application 62/476,287, filed Mar. 24, 2017, and entitled "SYSTEM AND METHOD FOR DELIVERING RADIOTHERAPY", which is incorporated herein by reference in its entirety for all purposes.

STATEMENT REGARDING FEDERALLY SPONSORED RESEARCH

This invention was made with government support under R44CA183390, and R43CA183390 awarded by the National Institutes of Health. The government has certain rights in this invention.

BACKGROUND

The present disclosure relates, in general, to external beam radiation therapy systems and methods, and more particularly to external beam radiation therapy systems and methods having a beam director with at least four degrees of freedom.

Conventional external beam radiation therapy, also referred to as "teletherapy," is commonly administered by directing beams of ionizing radiation produced by a linear accelerator ("LINAC") toward a defined target volume in a patient. Radiation dose with a specific profile can be built up in the target by shaping the beams into treatment fields using collimators and other devices, and irradiating the patient for certain amounts of time using the shaped beams. In preparing a radiation treatment plan, planning images, such as computed tomography ("CT"), are used to select beam configuration that optimize therapeutic effects and reduce radiation-induced side effects.

In addition, medical imaging can also be used concurrently with the delivery of radiation therapy in a technique called image-guided radiation therapy ("IGRT"). Using positional information from the images to supplement the radiation treatment plan, IGRT can improve the accuracy of the delivered radiation. This allows for radiation dose imparted to targeted regions to be escalated to achieve better outcomes, with reduced risk to healthy tissues.

Intensity modulated radiation therapy ("IMRT") is an external beam radiation therapy technique that utilizes computer planning software to produce a three-dimensional radiation dose map specific to locations, shapes and motion characteristics target and non-target structures in a patient. To do so, IMRT utilizes multiple beams that may be independently controlled in intensity and energy. Specifically, each beam includes a number of sub-beams or beamlets whose individual intensity can be varied to modulate the beam. Using this technique, specific regions within a targeted tumor, as well as other target and non-target structures in the patient's anatomy, can receive different radiation dose intensities.

The quality of radiation therapy delivered to a patient depends at least in part upon the spatial arrangement and intensity modulation of beams. When beam orientations are optimized, the quality of therapy can be significantly improved. However, optimized plans often require non-coplanar beams, which can be difficult to deliver using conventional LINACs. This is because these machines utilize gantries that have only one degree of rotational freedom. To address this, treatment plans often include patient couch repositioning. However, coordinating gantry and couch motion, along with imaging, can complicate treatment and introduce the potential for significant problems. For example, collisions, patient movement and difficulties with monitoring of the patient using imaging, can interfere with treatment and lead to possible equipment damage and patient injury. In addition, mechanical constraints on couch and gantry movements only provide a limited number of additional beam orientations. In many cases, such limited beam configurations can prevent clinicians from reaching the optimal plan quality and therefore the best treatment option.

Therefore, there is a need for improved systems and methods for delivering radiotherapy treatment.

SUMMARY

A radiotherapy system and method for delivering radiotherapy are provided. Features and advantages of the present disclosures may be appreciated from descriptions below.

In one aspect of the present disclosure, a radiotherapy system is provided. The radiotherapy system includes beam director comprising a radiation source configured to generate radiation for irradiating a patient, the beam director having at least four degrees of freedom of movement. The radiotherapy system also includes a controller configured to operate the beam director to irradiate the patient in accordance with a radiation treatment plan, wherein the radiation treatment plan is generated based on a solution space determined by the at least four degrees of freedom of movement of the beam director.

In another aspect of the present disclosure, a method for delivering a radiation treatment plan to a patient using a radiotherapy system is provided. The method includes generating, based on a dose prescription, a radiation treatment plan optimized from a solution space determined by a beam director of a radiotherapy system having at least four degrees of freedom of movement. The method also includes receiving imaging information acquired from a patient. The method further includes controlling the radiotherapy system to deliver the radiation treatment plan based on the imaging information.

DETAILED DESCRIPTION OF THE INVENTION

The present disclosure is directed to systems and methods for radiation therapy that can overcome one or more of the above-described drawbacks. Among other advantages, the present disclosure describes a novel approach for delivering radiotherapy that provides superior dosimetry and reduces treatment times as compared to conventional treatment methods.

Figure 1A:
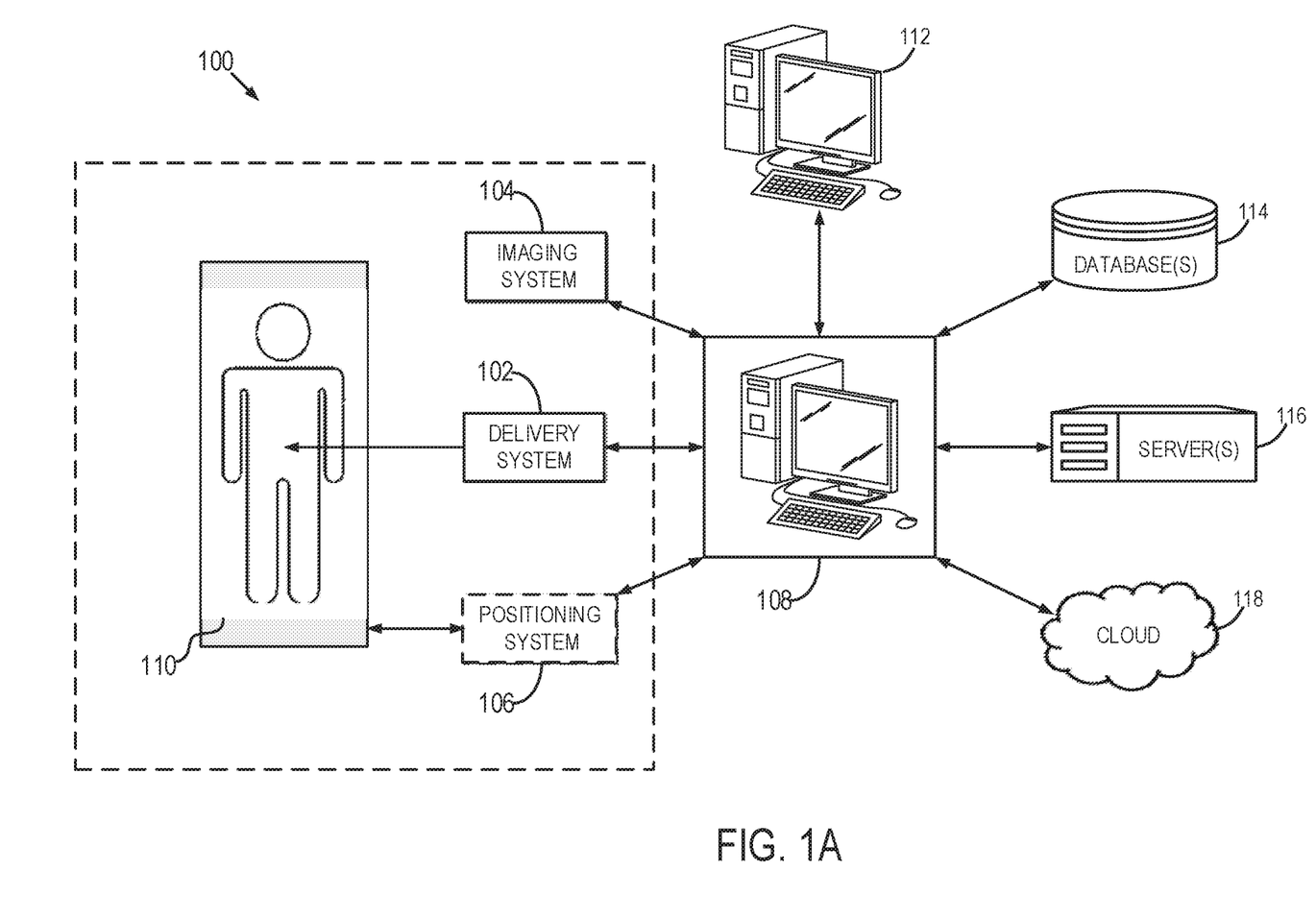
FIG. 1A is a schematic diagram of a radiotherapy system, in accordance with aspects of the present disclosure.

Referring particularly to FIG. 1A, the schematic diagram of a radiotherapy system 100, in accordance with aspects of the present disclosure, is shown. As shown, the radiotherapy system 100 may generally include a delivery system 102, an imaging system 104, and optionally a positioning system 106, each in communication with a treatment console 108. The delivery system 102 is configured to generate and direct radiation to a patient positioned on a treatment table 110, in accordance with a radiation treatment plan, where the treatment table 110 may be fixed or movable. The imaging system 104 may be configured to image the patient before, during or after treatment. Although shown in FIG. 1A as a separate system, in some embodiments, the imaging system 104 may be part of, or combined with, the delivery system 102. The positioning system 106 may be configured to position and orient the treatment table 110. In addition, the positioning system 106 may also be configured to move the patient to the imaging system 104.

The treatment console 108, or another suitable controller, may be configured to receive a radiation treatment plan from a planning workstation 112, or another location, such as a database 114, server 116 or cloud 118. Thereafter, the treatment console 108 may control the delivery system 102, imaging system 104 and optionally positioning system 106 to execute the radiation treatment plan. During treatment, the delivery system 102 builds radiation dose inside a patient to achieve dose distributions in accordance with the radiation treatment plan. The plan may include a number of treatment fields having various beam numbers, beam shapes or fluences, beam energies, beam orientations relative to the patient, and durations of exposure. In delivering the radiation treatment plan, the table 110 and patient may advantageously kept stationary, while the delivery system 102 is moved about the patient. This provides the ability to using beam angles that cover a significant portion of the 4π solid angle about the patient, including beam directions or beam orientations posterior in relation to the patient. In addition, errors associated with physically moving the table 110 and patient may also be avoided. Optionally, the radiation treatment plan may also be executed using a combination of table 110 and delivery system 102 movements.

Figure 1B:
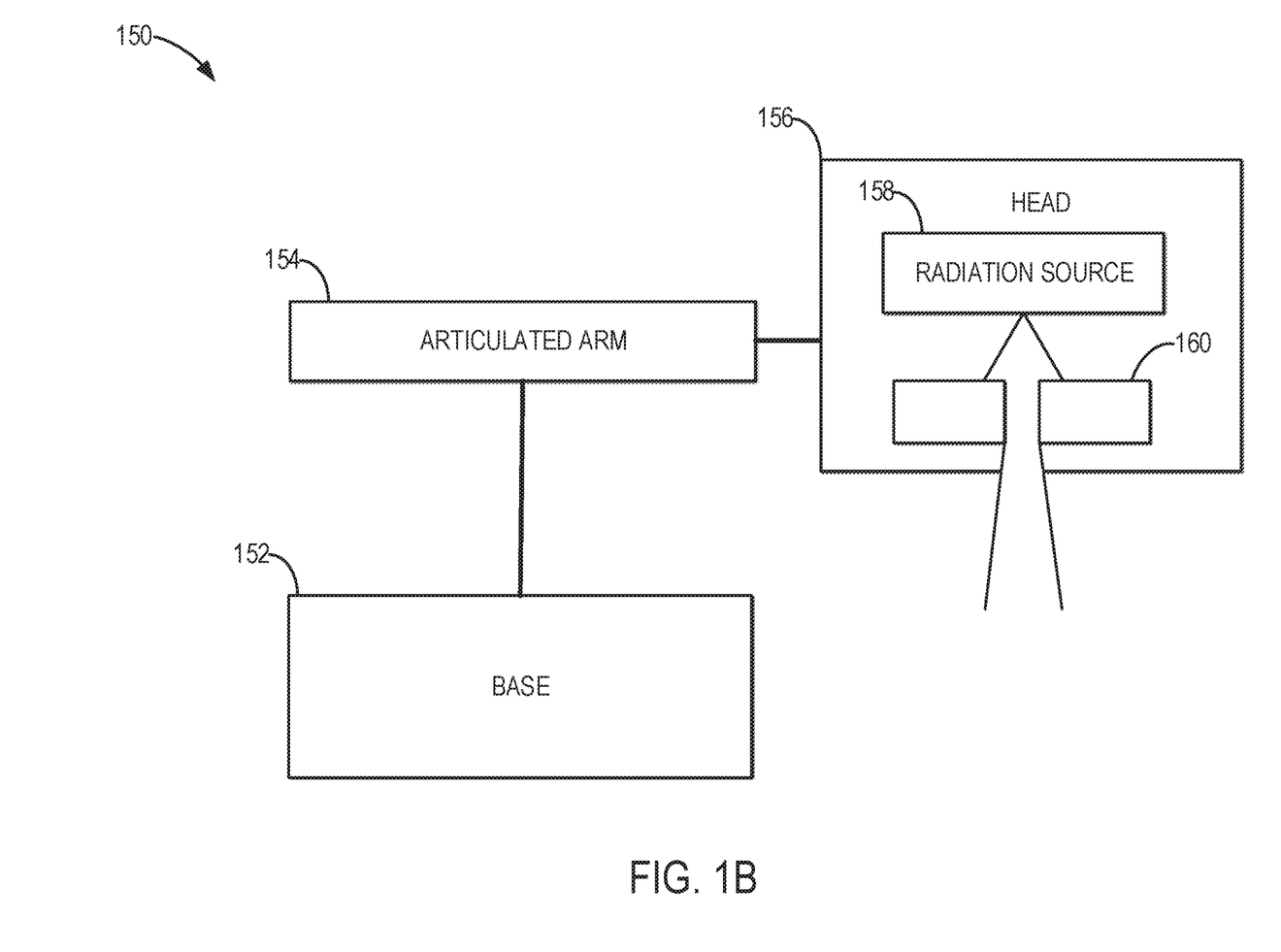
FIG. 1B is a schematic diagram of an example a beam director for the radiotherapy system of FIG. 1A.

In one embodiment, the delivery system 102 may include a beam director 150 that is configured to irradiate a patient from a plurality of directions, as shown schematically in FIG. 1B. The beam director 150 may include a base 152 providing support for the beam director 150, and an articulated arm 154 mechanically linked to the base 152. The beam director 150 may also include a treatment head 156 that is mechanically linked to the articulated arm 154. In some implementations, the beam director 150 may form, or be part of, a robotic system that may be controlled by the delivery system 102 or treatment console 108 of FIG. 1A.

Specifically, the treatment head 156 may be configured to house a radiation source 158, such as a linear accelerator ("LINAC"), as well as various elements and hardware for controlling radiation produced by the radiation source 158. For example, the treatment head 156 may include one or more collimators 160 (e.g., a multileaf collimator), and other elements, such as filters (e.g. flattening filters), foils (e.g. scattering foils), and waveguides. The radiation source 158 may be configured to generate radiation (e.g. X rays, electrons, and so on) having energies sufficient to produce desired therapeutic or radiobiological effects, such as the destruction of malignant tissue. More specifically, the energies of the radiation produced by the radiation source 158 are less than 6 MeV, although other energies may also be possible.

Although the radiation source 158 and collimator 160 are shown in FIG. 1B to be physically separated, in some implementations, the radiation source 158 and collimator 160 may be positioned directly adjacent to one another, or within a sufficiently close distance (e.g. less than 10 mm). In particular, the collimator 160 may be positioned adjacent to an output of the radiation source 158. In addition, the treatment head 156, and elements therein may be constructed with a reduced size and dimensions (as compared to conventional radiation treatment systems). This is advantageous for reducing the overall footprint of the delivery system 102. Also, a reduced size provides access to a patient from posterior angles, which are not accessible by existing robotic systems.

During the planning stage, a radiation treatment plan is often optimized to provide a conformal radiation dose to target tissues, in accordance with dosing prescriptions, while avoiding critical structures in a patient and reducing treatment time. As described, optimized treatment planning may often require the ability to provide coplanar and non-coplanar beam configurations relative to the patient. In addition, treatment field characteristics included in the radiation treatment plan, such as beam orientation and fluence, are determined by the movement capability of particular system utilized. Therefore, in some aspects, a radiation treatment plan delivered using the radiotherapy system 100 may be optimized from a very large solution space.

Therefore, at least a portion of the beam director 150 (e.g. the treatment head 156) may have freedom of movement of at least four and up to six degrees of freedom. For instance, the articulated arm 154 may include at least two joints providing the beam director 150 flexibility of movement spanning a significant portion of a 4π solid angle about the patient (e.g. greater than about 60% of the 4π solid angle). The ability to cover a large portion of the solid angle represents a significant improvement over previous C-arm gantry radiotherapy systems, which typically can access around 15%-60% of the solid angle. In addition, the movement capability of the beam director 150 allows for varied source-to-tumor distances, or source-to-axis distances ("SADs"), during treatment. To provide the full ability to direct or orient beams around a patient as necessary, in some implementations, the beam director 150 may be configured to move the treatment head 156 along three spatial axes (e.g. x, y and z axes), to orient the treatment head 156 using three rotational axes (e.g. yaw, pitch and roll), or achieve movement using a combination thereof.

Figure 1C:
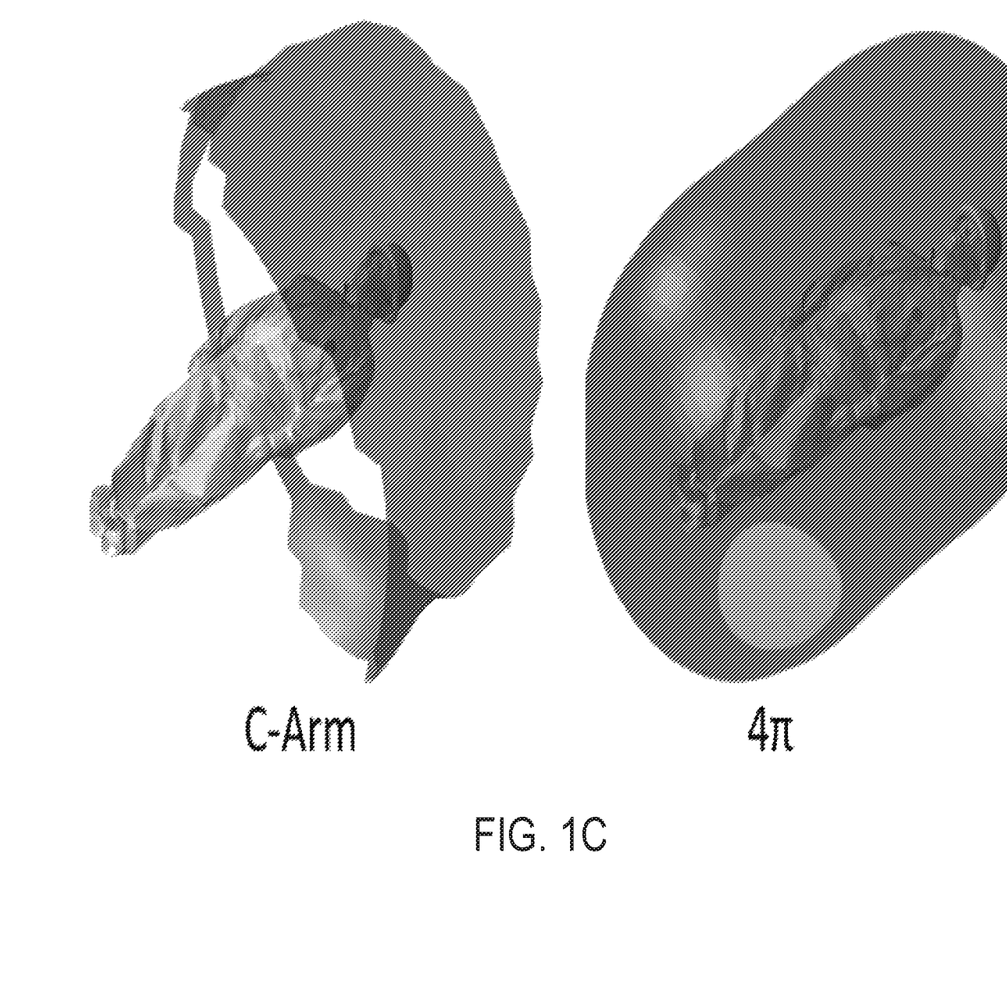
FIG. 1C is an illustration comparing the solution space for a conventional C-arm radiotherapy system and the solution space for a radiotherapy system, in accordance with aspects of the present disclosure.

To visually illustrate this point, FIG. 1C shows a comparison between the solution space for a conventional C-arm gantry radiotherapy system (left side), and a solution space for a radiotherapy system of the present disclosure (right side). As appreciated from the figure, having movement capability with at least four degrees of freedom allows coverage of the full solid angle access about the patient. By contrast, the C-arm radiotherapy system is substantially limited.

The ability to cover a significant portion of the 4π solid angle can reduce the need for deep penetration of radiation into a patient. Accordingly, the beam director 150 of FIG. 1B need not require a high-energy radiation source. Rather, the radiation source 158 may include low-energy source or accelerator configured to provide low-energy radiation (i.e. less than conventional 6 MeV). In fact, and unexpectedly, results show that lower energy radiation can provide superior performance. This may be due, in part, to the decreased size of the lateral penumbra, and increased dose compactness produced by the beam director 150. In addition, lower energy radiation reduces the size and weight requirements of the radiation source 158, and simplifies the design of the collimator 160. Furthermore, lower energies also reduce shielding requirements for the treatment head 156 and treatment room.

Referring again to FIG. 1A, the planning workstation 112 may be utilized to generate a radiation treatment plan based on dosimetric prescriptions and imaging information obtained from a subject. As described, generating the plan include selecting appropriate treatment fields, which can vary in number, duration, shape or fluence, energy and orientation relative to the patient, to optimize patient outcomes. In some applications, variable SADs may be needed to avoid an undesired compromise between field size and intensity modulation resolution. Furthermore, variable SADs allow for both larger and smaller tumors to be treated optimally. However, combining a large number of options afforded by the significant portion of a 4π solid angle, with various radiation field parameters (e.g. duration, shape, energy, direction, fluence, SADs, and others) necessitates an optimization algorithm capable of taking into account a large solution space. To this end, the planning workstation 112 may be configured to perform an integrated beam orientation and optimization method to generate the radiation treatment plan. In some aspects, treatment field characteristics, such as beam orientation, may be optimized for both dosimetry and efficiency. As an example, an optimization approach developed by the inventors and described in PCT/US2016/020234, which is incorporated herein by reference, in its entirety, may be used, although other approaches may also be possible.

In some implementations, the planning workstation 112 may include one or more processors configured to execute non-transitory software or programming that includes steps for carrying out an optimization algorithm in a solution space determined by a radiotherapy system, and more specifically a beam director, having at least four degrees of freedom of movement. As described, such solution space may cover 60% or more of the 4π solid angle about the patient. More specifically, the solution space covers at least 90% of the 4π solid angle. In some implementations, at least one processor in the planning workstation 112 may include hardwired instructions or programming for carrying out an optimization algorithm, as described. Such processor would therefore be a special-purpose processor, by way of its specialized programming.

Figure 2A:
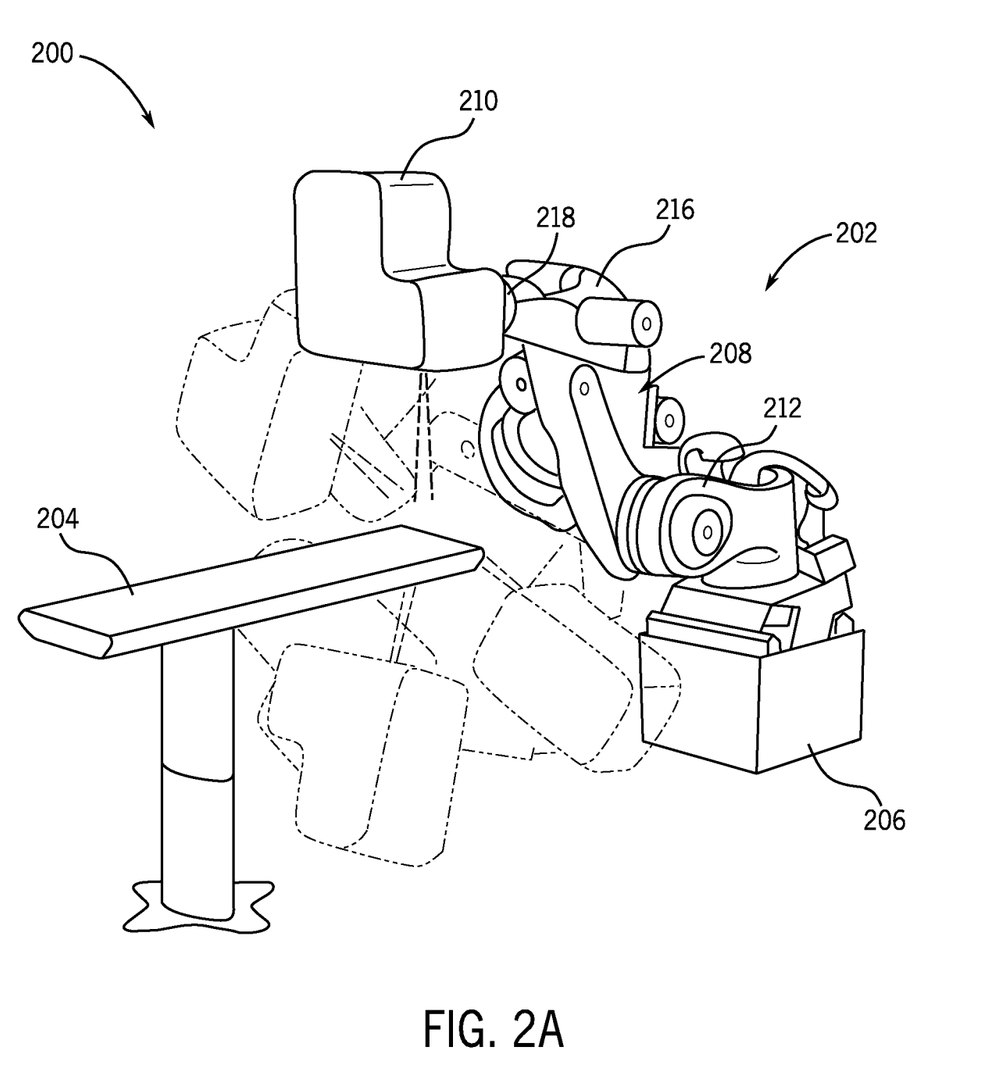
FIG. 2A is an image showing one example of the radiotherapy system of FIG. 1A.
Figure 2B:
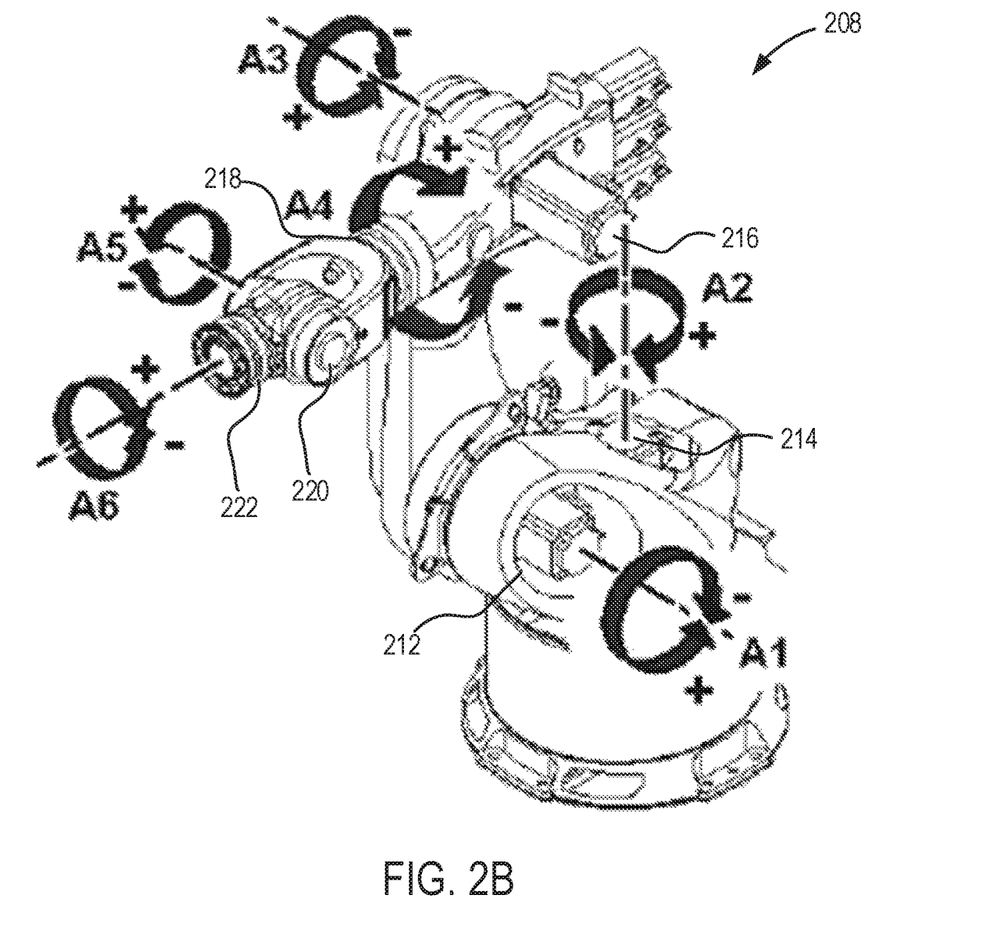
FIG. 2B is an illustration showing one example of an articulated arm, in accordance with aspects of the present disclosure.

By way of non-limiting example, FIG. 2A-B illustrate one embodiment of a radiotherapy system 200, in accordance with aspects of the present disclosure. The radiotherapy system 200 includes a beam director 202 and patient table 204. As shown, the patient table 204 is fixed. The beam director 202 includes a base 206, an articulated arm 208 and a treatment head 210. As described, the treatment head 210 may include a radiation source (i.e. a LINAC), a collimator (i.e. a multi-leaf collimator), and other elements and circuitry. The motion of beam director 202 can be controlled by a beam director controller, which can communicate with one or more operator workstations or computers. As appreciated from FIGS. 2A and 2B, the radiotherapy system 200 allows beam directions that span up to a full solid angle about the patient.

Referring specifically to FIG. 2B, the articulated arm 208 may include a number of pivoting points or joints allowing up to six degrees of freedom of movement of the beam director 202, and radiation source, about the patient. As shown, a first joint 212, a second joint 214, a third joint 216, a fourth joint 218, a fifth joint 220, and a sixth joint 222 allow rotation of the articulated arm 208 about a first axis A1, a second axis A2, a third axis A3, a fourth axis A4, a fifth axis A5, and a sixth axis A6, respectively.

Figure 3:
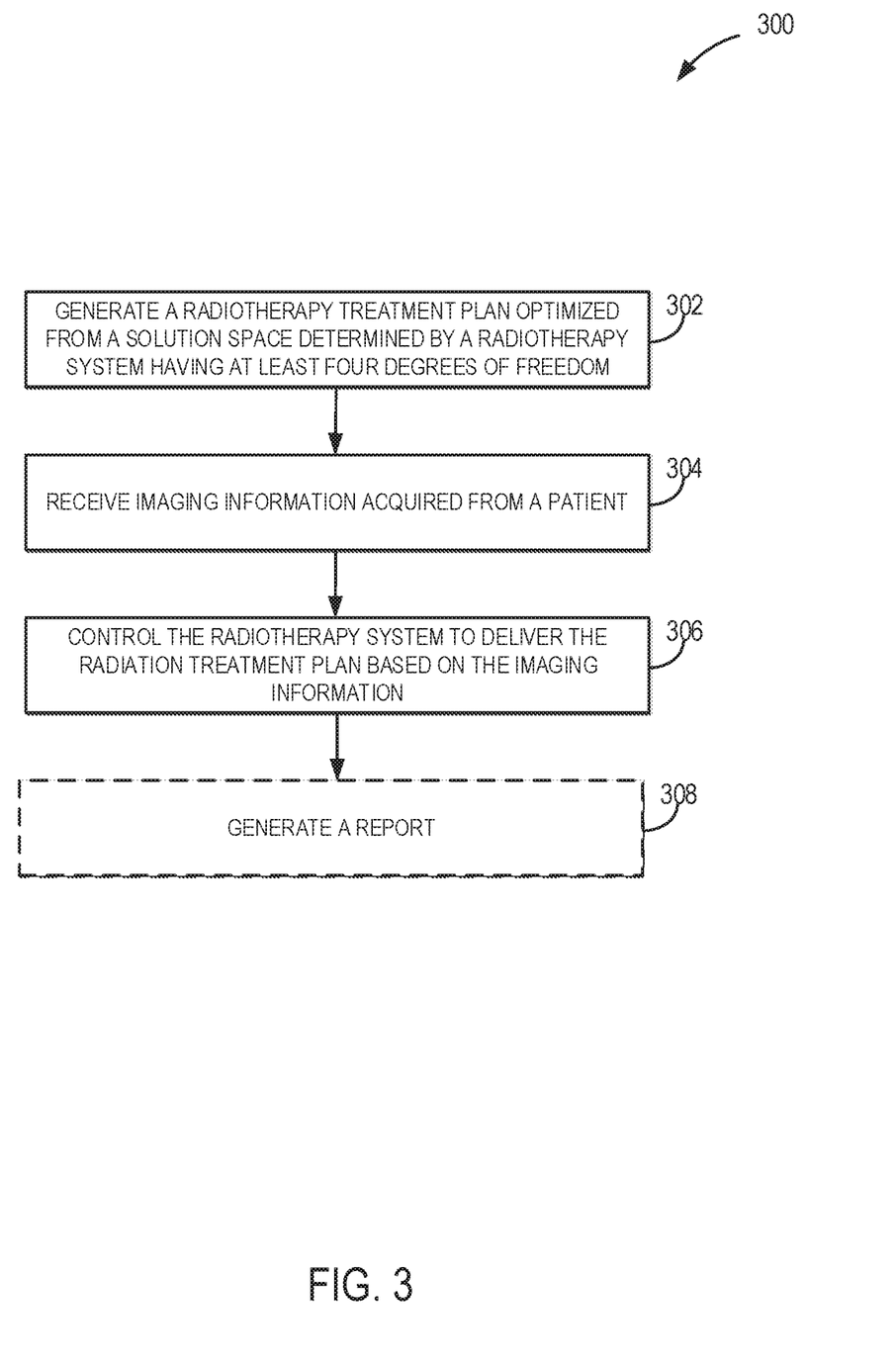
FIG. 3 is a flowchart setting forth steps of a process, in accordance with aspects of the present disclosure.

Turning now to FIG. 3, a flowchart setting forth steps of a process 300 in accordance with aspects of the present disclosure is shown. The process 300, or various steps therein, may be carried on or using any suitable device, apparatus or system, such as the radiotherapy system described with reference to FIG. 1A. In some implementations, the steps of the process 300 may be performed by one or more processors or computers configured to execute programming or instructions stored in non-transitory computer readable media. The processor(s) may be include general-purpose processors, as well as application-specific processors having programming or executable instructions hardwired therein.

The process 300 may begin at process block 302 with generating a radiation treatment plan. As described, the radiation treatment plan may be optimized from a solution space that is determined by the delivery system of a radiotherapy system, and more particularly, a beam director having at least four degrees of freedom of movement. As such, an optimization algorithm may be executed at process block 302 to generate the radiation treatment plan. In particular, the optimization algorithm may be configured to select beam configurations achieving dosimetric prescriptions based on the solution space determined by the beam director. In some aspects, the optimization algorithm may optimize a dosimetry and an efficiency of delivery beams in the radiation treatment plan.

In one non-limiting example, the solution space covers at least 60% of the 4π solid angle about the patient, and more specifically at least 90% of the 4π solid angle. In generating the radiation treatment plan, the various movements performed or paths navigated by the beam director may also be determined. Such movements and paths may be optimized to minimize patient treatment time and treatment efficiency, as well as to avoid collisions with the patient, the patient table and other equipment present during treatment.

Then at process block 304, imaging information acquired from a patient prior to treatment may be received. Such imaging information may be in the form of radiographs, CT's, MRI, video and other imaging information. In some aspects, the radiation treatment plan may be adapted based on analysis of the imaging information received at process block 302. For example, a position, alignment or orientation of the patient may be determined based on the imaging information and used to adapt or correct the radiation treatment plan. In some aspects, correction of patient position, alignment or orientation may be performed without physically moving the patient or patient table.

Then at process block 304, the radiation treatment plan is delivered by controlling the radiotherapy system based on the imaging information. In some aspects, the radiation treatment plan may be delivered using a delivery system that is configured to selectively access a 4π solid angle about the patient.

A report, in any form, may then be optionally generated, as indicated by process block 308. For example, the report may indicate a status or completion of treatment field(s), a treatment progress, treatment interruptions or errors, positioning of the delivery system and components therein, and so on.

Figure 4A:
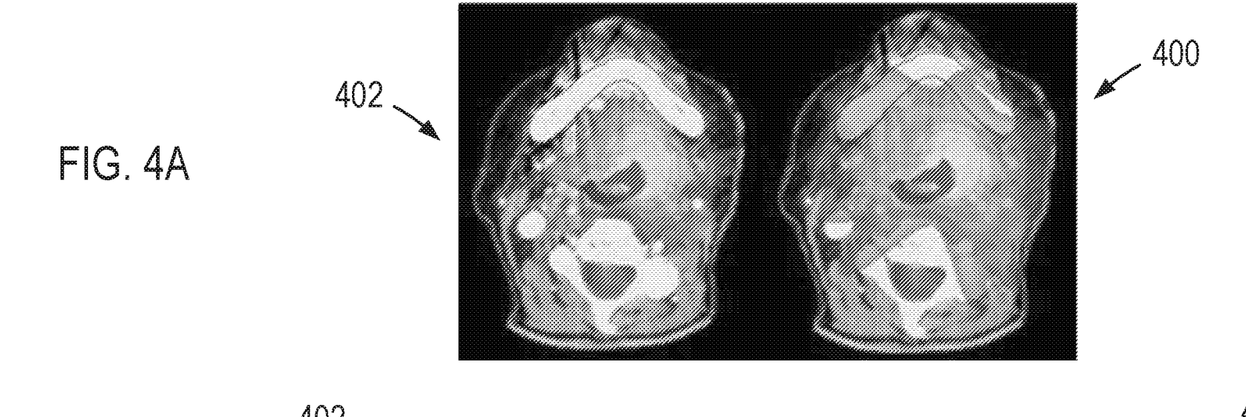
FIG. 4A are images comparing dose distributions, optimized for conventional radiotherapy systems and a radiotherapy system according to the present disclosure, for an example treatment head and neck case.
Figure 4B:
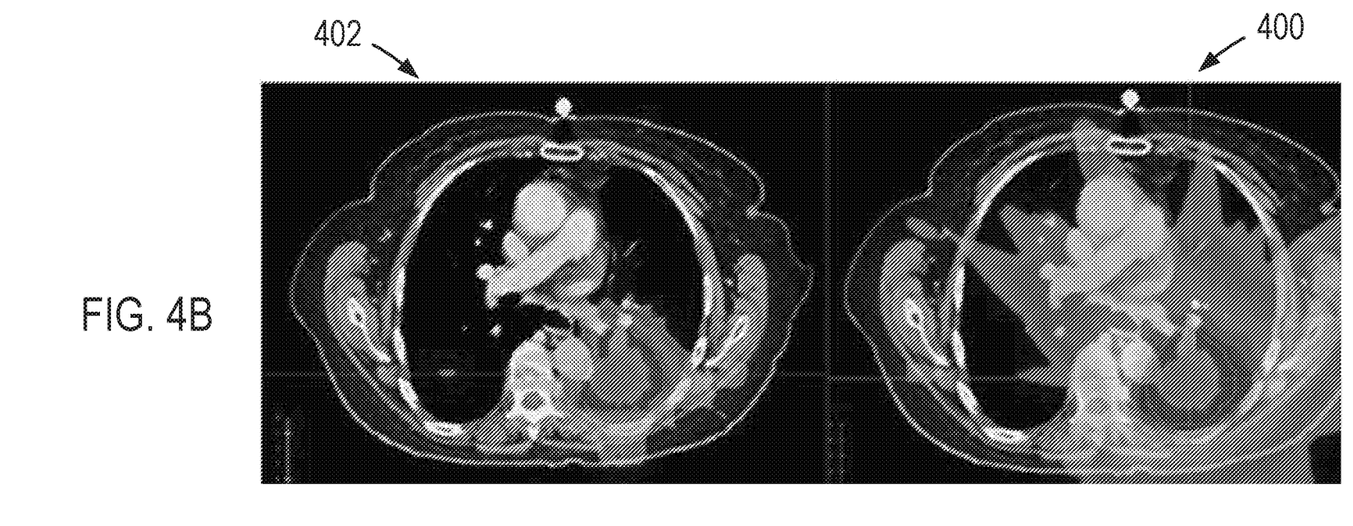
FIG. 4B are images comparing dose distributions, optimized for conventional radiotherapy systems and a radiotherapy system according to the present disclosure, for an example lung case.

FIGS. 4A and 4B illustrates a comparison of dose distributions for example head and neck and lung cases. The dose distributions were optimized for a conventional radiotherapy system, as indicated by label 400, and for a radiotherapy system, in accordance with aspects of the present disclosure, as indicated by label 402. As appreciated from the figures, the present approach provides more conformal distributions compared to the previous technique, which would results in reduced radiation exposure to non-targeted tissues.

The system and method for delivering radiotherapy described herein provide a number of advantages over existing radiotherapy systems. First, the dosimetry achievable herein is superior to methods that are limited to coplanar beam configurations. For example, a 20-40% normal organ dose reduction can be achieved using the approach described herein. Second, compared to coplanar plans generated for radiotherapy systems having C-arm gantries, treatment time can be reduced from 50 minutes to less than 15 minutes using the present approach. Third, patient secondary movements, due to table motion, can be minimized by keeping the patient static during the entire treatment. Third, optimizing the beam orientation and fluence maps together results in significantly superior dosimetry as shown in FIGS. 4A-4B. Fourth, the reduced size of the treatment head of a beam director (i.e., the LINAC treatment head) allows full access to the posterior beam angles that can often be critical to plan quality. Finally, utilizing an optimization algorithm that can address both small and large tumors provides increased flexibility for the radiotherapy system described here, which can increase the number of patients that can be treated in a day (e.g., 3-4 times more patients) as compared to conventional radiotherapy systems.

Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A radiotherapy system comprising:
a beam director comprising a radiation source configured to generate radiation for irradiating a patient, the beam director having at least four degrees of freedom of movement; and
a controller configured to operate the beam director to irradiate the patient in accordance with a radiation treatment plan,
wherein the radiation treatment plan is generated based on a solution space determined by the at least four degrees of freedom of movement of the beam director, and
wherein the radiation treatment plan includes a beam orientation that is posteriorly angled relative to the patient so that a treatment head of the radiotherapy system is configured to be positioned below a table that supports the patient.

2. The radiotherapy system of claim 1, wherein the radiation source comprises a linear accelerator.

3. The radiotherapy system of claim 1, wherein the beam director comprises a base providing support to the beam director.

4. The radiotherapy system of claim 3, wherein the beam director further comprises an articulated arm extending from the base and mechanically linked to the base.

5. The radiotherapy system of claim 4, wherein the articulated arm comprises at least two joints configured to provide the beam director the at least four degrees of freedom of movement.

6. The radiotherapy system of claim 4, wherein the beam director further comprises a treatment head that houses the radiation source, the treatment head being mechanically linked to the articulated arm.

7. The radiotherapy system of claim 6, wherein the treatment head further comprises a collimator positioned adjacent to an output of the radiation source.

8. The radiotherapy system of claim 1, wherein the solution space covers at least 90% of a 4π solid angle about the patient.

9. The radiotherapy system of claim 1, wherein the controller is further configured to operate the beam director to irradiate the patient from directions posterior in relation to the patient.

10. The radiotherapy system of claim 1, wherein the controller is further configured to operate the beam director to irradiate the patient and deliver the radiation treatment plan while the patient is stationary.

11. The radiotherapy system of claim 1, wherein the radiation source provides radiation with energies less than 6 Mega electron-volts (MeV) to the patient.

12. The radiotherapy system of claim 1, wherein the treatment head is configured to be positioned below the patient.

13. The radiotherapy system of claim 12, further comprising a patient table that is fixed during treatment, and wherein the beam director includes a treatment head that provides the radiation to the patient, and
wherein with the treatment head providing a beam of radiation along the beam orientation and with the patient supported by the patient table, the treatment head is configured to be positioned below the patient.

14. A method for delivering a radiation treatment plan to a patient using a radiotherapy system, the method comprising;
generating, based on a dose prescription, a radiation treatment plan optimized from a solution space that covers at least 60% of a 4π solid angle about the patient to define a plurality of beam orientations relative to the patient that are each different, the radiation treatment plan determined by a beam director of a radiotherapy system having at least four degrees of freedom of movement;
receiving imaging information acquired from a patient;
controlling the radiotherapy system to deliver the radiation treatment plan based on the imaging information.

15. The method of claim 14, wherein the method further comprises executing an optimization algorithm to generate the radiation treatment plan, the optimization algorithm configured to select beam configurations based on the solution space determined by the beam director.

16. The method of claim 15, wherein the method further comprises executing the optimization algorithm to optimize a dosimetry and an efficiency of delivering beams in the radiation treatment plan.

17. The method of claim 14, wherein the solution space covers at least 90% of the $4\pi$ solid angle about the patient.

18. The method of claim 14, wherein the method further comprises generating the radiation treatment plan using a variable source-to-axis distance ("SAD").

19. The method of claim 14, wherein the radiotherapy system includes a treatment head that provides radiation to the patient, and which is configured to be positioned below the patient.

20. The method of claim 14, wherein the radiotherapy system has a radiation source that provides radiation with energies less than 6 Mega electron-volts (MeV) to the patient.

* * * * *